(12) United States Patent (10) Patent No.: US 12,653,203 B2
Neel et al. (45) Date of Patent: Jun. 16, 2026

(54) PORTABLE FOOD STERILIZATION ASSEMBLY

(71) Applicants:Christopher Neel, San Tan Valley, AZ (US); Tawny Neel, San Tan Valley, AZ (US)

(72) Inventors: Christopher Neel, San Tan Valley, AZ (US); Tawny Neel, San Tan Valley, AZ (US)

( * ) Notice: Subject to any disclaimer, the term of this patent is extended or adjusted under 35 U.S.C. 154(b) by 381 days.

(21) Appl. No.: 18/198,841

(22) Filed: May 17, 2023

(65) Prior Publication Data

US 2024/0381904 A1 Nov. 21, 2024

(51) Int. Cl.

| | |
|---|---|
| *A23B 2/00* | (2025.01) |
| *A23B 2/53* | (2025.01) |
| *B65D 81/28* | (2006.01) |
| *A61L 2/10* | (2006.01) |
| *B65D 81/38* | (2006.01) |

(52) U.S. Cl.
CPC ................ *A23B 2/001* (2025.01); *A23B 2/53* (2025.01); *A61L 2/10* (2013.01); *B65D 81/28* (2013.01); *B65D 81/3813* (2013.01)

(58) Field of Classification Search
CPC .. A61L 2/10; A23B 2/53; A23B 2/001; B65D 81/28
See application file for complete search history.

(56) References Cited

U.S. PATENT DOCUMENTS

| | | | | |
|---|---|---|---|---|
| 7,205,016 | B2 * | 4/2007 | Garwood | ................ A23L 13/00 426/118 |
| 7,984,997 | B1 | 7/2011 | Sandberg | |
| 8,277,734 | B2 * | 10/2012 | Koudymov | ............... A61L 2/10 436/164 |
| D744,786 | S | 12/2015 | Bagwell | |
| 9,726,424 | B1 | 8/2017 | Sandberg | |
| 10,088,144 | B1 | 10/2018 | Sandberg | |
| 10,203,154 | B1 * | 2/2019 | Wyatt | ..................... F21V 23/04 |
| 11,187,451 | B2 | 11/2021 | Akinci | |
| D1,055,640 | S * | 12/2024 | Sandmæl | ........................ D7/605 |
| 2005/0178984 | A1 * | 8/2005 | Brickley | ................. H01J 61/52 250/504 R |
| 2005/0258108 | A1 * | 11/2005 | Sanford | .................. C02F 1/325 210/748.11 |

(Continued)

FOREIGN PATENT DOCUMENTS

WO WO2018141620 9/2018

*Primary Examiner* — Wyatt A Stoffa

(57) ABSTRACT

A portable food sterilization assembly includes an ice chest defining an interior space to contain food items. The ice chest is comprised of a thermally insulating material to inhibit thermal communication between the interior space and ambient air. A lid is hingedly coupled to the ice chest for opening or closing the interior space. The lid is comprised of a thermally insulating material to inhibit thermal communication between the interior space and ambient air. A plurality of ultraviolet light emitters is integrated into the ice chest to emit ultraviolet light into the interior space for sterilizing the interior space of the ice chest thereby sterilizing food items contained in the interior space. A respective one of the plurality of ultraviolet light emitters is integrated into the lid to emit ultraviolet light into the interior space of the ice chest thereby sterilizing food items contained in the interior space.

2 Claims, 4 Drawing Sheets

(56)  References Cited

U.S. PATENT DOCUMENTS

| | | | | |
|---|---|---|---|---|
| 2007/0031281 A1* | 2/2007 | Stevens | A61L 2/10 | |
| | | | | 422/24 |
| 2009/0189085 A1* | 7/2009 | Rogers | A23B 2/503 | |
| | | | | 426/240 |
| 2009/0280035 A1* | 11/2009 | Koudymov | A61L 2/12 | |
| | | | | 422/119 |
| 2012/0006995 A1* | 1/2012 | Greuel | C02F 1/325 | |
| | | | | 250/455.11 |
| 2013/0104579 A1 | 5/2013 | Zhou | | |
| 2014/0013789 A1* | 1/2014 | Conrad | F25D 3/08 | |
| | | | | 62/331 |
| 2014/0060095 A1* | 3/2014 | Shur | A61L 2/10 | |
| | | | | 250/455.11 |
| 2019/0201570 A1* | 7/2019 | Dobrinsky | G01N 21/8806 | |
| 2021/0338865 A1* | 11/2021 | Lee | B65B 55/08 | |
| 2022/0079379 A1* | 3/2022 | Ganahl | A47J 36/10 | |
| 2022/0111083 A1* | 4/2022 | Johnson | A61L 2/10 | |
| 2022/0142388 A1* | 5/2022 | Foster | A47G 29/141 | |
| 2022/0249718 A1* | 8/2022 | Rifkin | A47L 9/30 | |
| 2022/0313012 A1* | 10/2022 | Ganahl | B65D 25/32 | |
| 2023/0012667 A1* | 1/2023 | Asimus | A61L 2/26 | |
| 2023/0055756 A1* | 2/2023 | Brown | A61L 2/10 | |
| 2024/0188698 A1* | 6/2024 | Johnson | A45C 11/20 | |

* cited by examiner

PORTABLE FOOD STERILIZATION ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to sterilization devices and more particularly pertains to a new sterilization device for sterilizing food and beverages contained in an ice chest. The device includes an ice chest, a plurality of ultraviolet light emitters integrated into the ice chest and a plurality of lenses which covers each of the ultraviolet light emitters to protect the ultraviolet light emitters from damage.

(2) Description of Related Art Including Information Disclosed Under 37 CFR 1.97 and 1.98

The prior art relates to sterilization devices including a variety of ice chest devices that each has a light emitter for illuminating an interior of the ice chest and a plurality of refrigerators that each has an ultraviolet light emitter for sterilizing an interior of the refrigerator. In no instance does the prior art disclose an ice chest with a plurality of ultraviolet light emitters for sterilizing an interior of the ice chest.

BRIEF SUMMARY OF THE INVENTION

An embodiment of the disclosure meets the needs presented above by generally comprising an ice chest defining an interior space to contain food items. The ice chest is comprised of a thermally insulating material to inhibit thermal communication between the interior space and ambient air. A lid is hingedly coupled to the ice chest for opening or closing the interior space. The lid is comprised of a thermally insulating material to inhibit thermal communication between the interior space and ambient air. A plurality of ultraviolet light emitters is integrated into the ice chest to emit ultraviolet light into the interior space for sterilizing the interior space of the ice chest thereby sterilizing food items contained in the interior space. A respective one of the plurality of ultraviolet light emitters is integrated into the lid to emit ultraviolet light into the interior space of the ice chest thereby sterilizing food items contained in the interior space.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figures 1, 2:
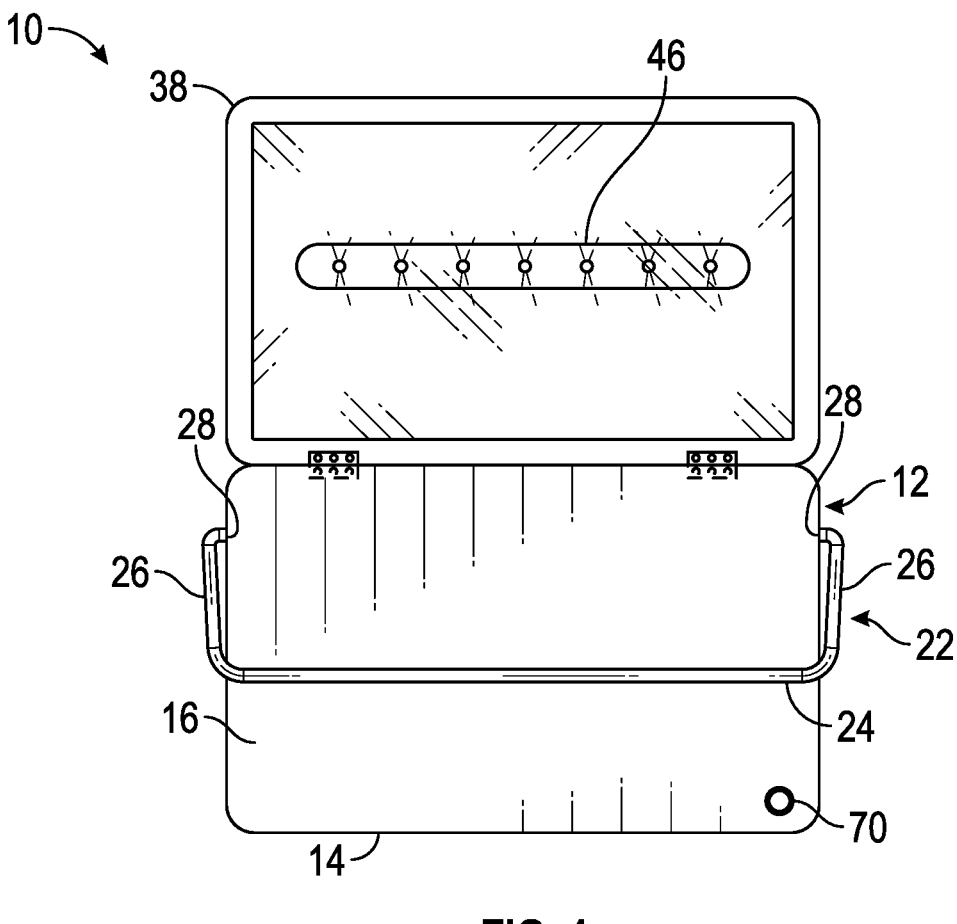
FIG. 1 is a front view of a portable food sterilization assembly according to an embodiment of the disclosure.
FIG. 2 is a back view of an embodiment of the disclosure.
Figure 3:
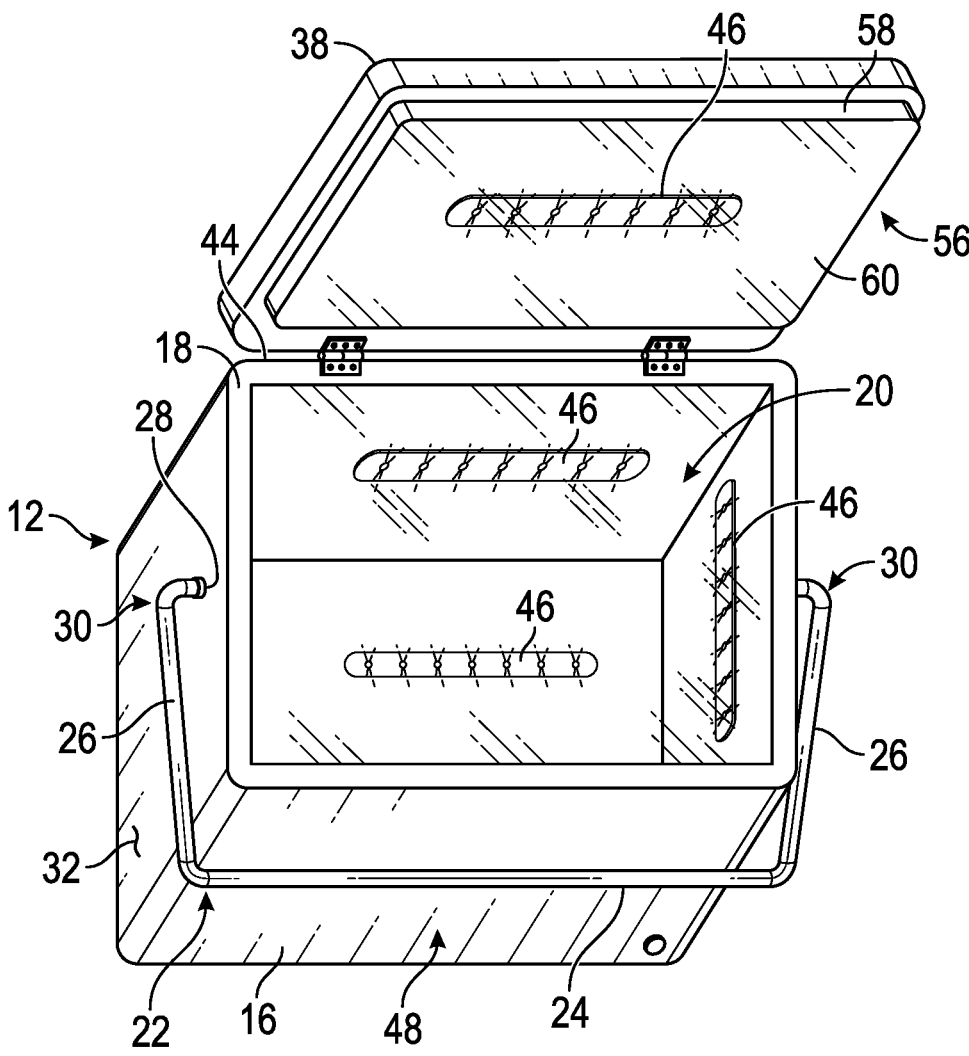
FIG. 3 is a top perspective view of an embodiment of the disclosure.
Figure 4:
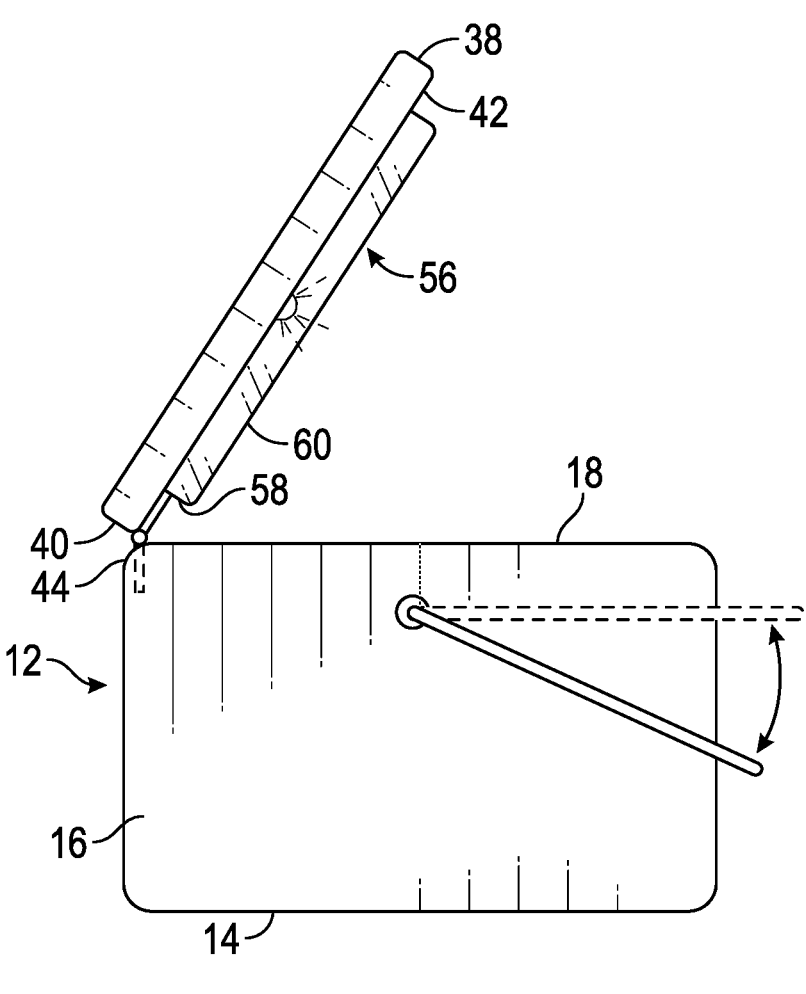
FIG. 4 is a right view of an embodiment of the disclosure.
Figure 5:
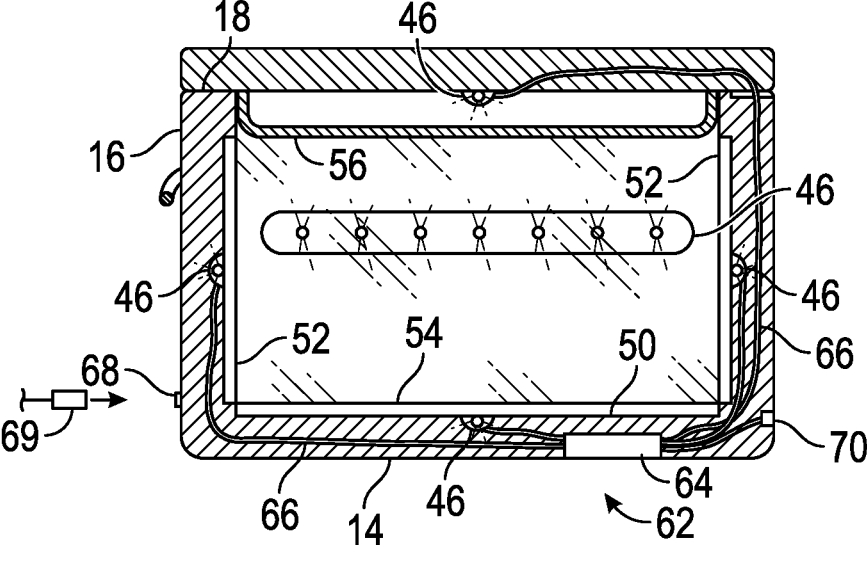
FIG. 5 is a cross sectional view taken along line 5-5 of FIG. 2 of an embodiment of the disclosure.
Figure 6:
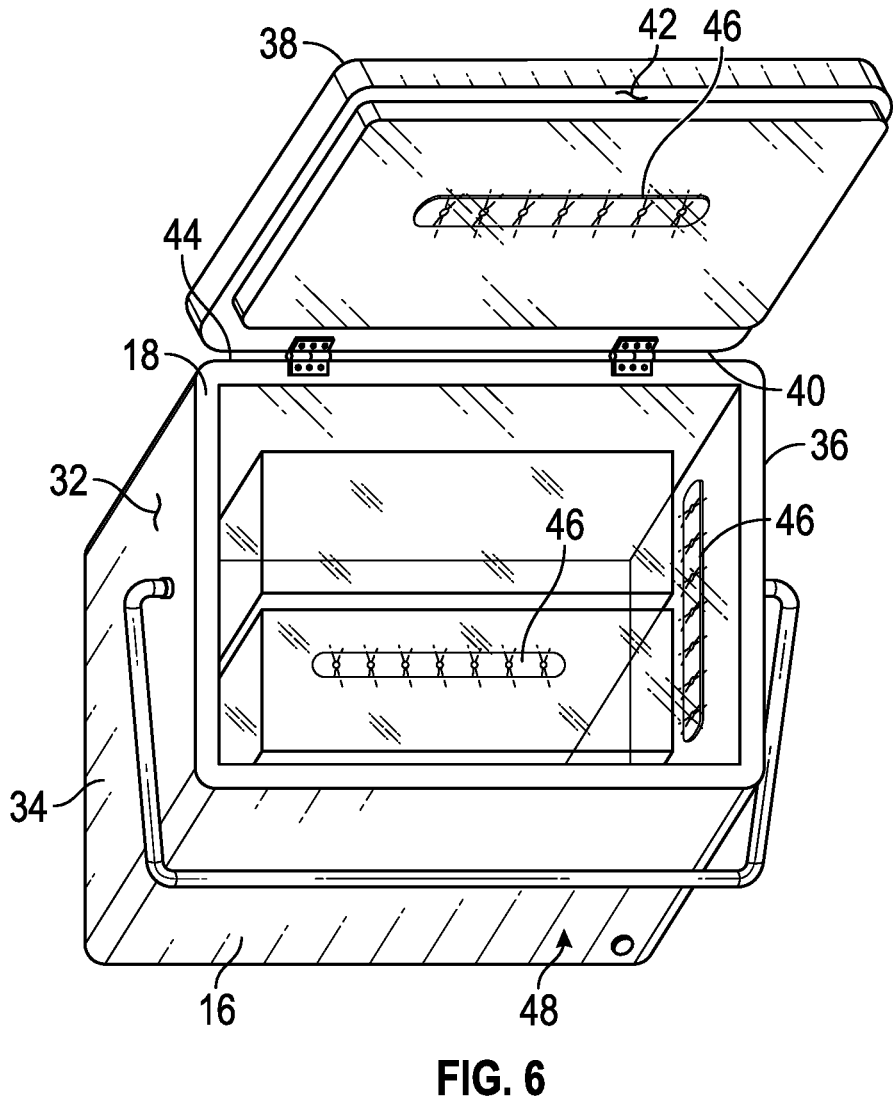
FIG. 6 is a perspective in-use view of an embodiment of the disclosure.

With reference now to the drawings, and in particular to FIGS. 1 through 6 thereof, a new sterilization device embodying the principles and concepts of an embodiment of the disclosure and generally designated by the reference numeral 10 will be described.

As best illustrated in FIGS. 1 through 6, the portable food sterilization assembly 10 generally comprises an ice chest 12 which defines an interior space to contain food items. The ice chest 12 is comprised of a thermally insulating material to inhibit thermal communication between the interior space and ambient air. The ice chest 12 has a bottom wall 14 and an outer wall 16 extending upwardly from the bottom wall 14 and the outer wall 16 has a top edge 18 defining an opening 20 in the interior space defined by the ice chest 12. A handle 22 is included which has a central member 24 extending between and being perpendicularly oriented with a pair of outward members 26. Each of the outward members 26 has a distal end 28 and a bend 30 that is spaced from the distal end 28 such that the distal end 28 of each of the outward members 26 is directed toward each other. The distal end 28 of each of the outward members 26 is rotatably coupled to an outer surface 32 of the outer wall 16 of the ice chest 12 corresponding to a respective one of the first lateral side 34 and the second lateral side 36 of the outer wall 16. The handle 22 is positionable in a carrying position having the central member 24 being spaced upwardly from the ice chest 12 such that the central member 24 can be gripped for carrying the ice chest 12. Additionally, the handle 22 is positionable in a stored position having the central member 24 resting against the outer wall 16 of the ice chest 12.

A lid 38 is hingedly coupled to the ice chest 12; the lid 38 is positionable in a closed position for closing the interior space and the lid 38 is positionable in an open position for exposing the interior space. The lid 38 is comprised of a thermally insulating material to inhibit thermal communication between the interior space and ambient air. Additionally, the lid 38 has a rear edge 40 and a bottom surface 42 and the rear edge 40 is hingedly coupled to a back side 44 of the top edge 18 of the outer wall 16 of the ice chest 12.

A plurality of ultraviolet light emitters 46 is provided and respective ones of the plurality of ultraviolet light emitters 46 is integrated into the ice chest 12. In this way each of the respective plurality of ultraviolet light emitters 46 can emit ultraviolet light into the interior space for sterilizing the interior space of the ice chest 12 thereby sterilizing food items contained in the interior space. Thus, individuals that will consume the food items will not become ill due to bacterial contamination of the food items. The food items may include uncooked meat, vegetables, beverage containers and any other food items typically consumed at a picnic, for example, or other outdoor event. Furthermore, each of the plurality of ultraviolet light emitters 46 may comprise a light emitting diode, an incandescent bulb or any other type of electronic light emitter that emits light in the ultraviolet wavelength ranging between 200.0 and 280.0 nm and which has an output intensity sufficient to kill bacteria.

A respective one of the plurality of ultraviolet light emitters 46 is integrated into the lid 38 to emit ultraviolet light into the interior space of the ice chest 12 thereby sterilizing food items contained in the interior space. Respective ones of the ultraviolet light emitters 46 associated with the ice chest 12 is integrated into an interior surface of the outer wall 16. Furthermore, each of the ultraviolet light emitters 46 associated with the outer wall 16 of the ice chest 12 is integrated into a respective one of a front side 48, the first lateral side 34 and the second lateral side 36 of the outer wall 16 of the ice chest 12. A respective one of the ultraviolet light emitters 46 associated with the ice chest 12 is integrated into a top surface 50 of the bottom wall 14 of the ice chest 12. Additionally, the ultraviolet light emitter 46 associated with the lid 38 is integrated into the bottom surface 42 of the lid 38.

A plurality of first lenses 52 is included and each of the plurality of first lenses 52 is integrated into the interior surface of the outer wall 16 of the ice chest 12. Each of the plurality of first lenses 52 is integrated into a respective one of the first lateral side 34, the second lateral side 36 and the front side 48 of the outer wall 16 of the ice chest 12 such that each of the plurality of first lenses 52 covers a respective one of the plurality of ultraviolet light emitters 46. Each of the first lenses 52 is comprised of a translucent material to pass light through the first lenses 52. A second lens 54 is integrated into the top surface 50 of the bottom wall 14 of the ice chest 12 such that the second lens 54 covers the ultraviolet light emitter associated with the lid 38. Additionally, the second lens 54 is comprised of a translucent material to pass light through the second lens 54.

A third lens 56 is integrated into the bottom surface 42 of the lid 38 such that the third lens 56 covers the ultraviolet light emitter 46 associated with the lid 38. The third lens 56 has a perimeter wall 58 that is perpendicularly oriented with the bottom surface 42 of the lid 38 and a distal wall 60 that is spaced from and lies on a plane which is oriented parallel to the bottom surface 42 of the lid 38. The third lens 56 is comprised of a translucent material to pass light through the third lens 56 and the perimeter wall 58 is spaced inwardly from a perimeter edge of the lid 38 such that the third lens 56 extends into the interior space of the ice chest 12 when the lid 38 is in the closed position. Each of the first lenses 52, the second lens 54 and the third lens 56 may be comprised of polycarbonate, acrylic or any other type of translucent and resilient material that is unlikely to be damaged or shattered by beverage containers and food containers.

A power supply 62 is integrated into the ice chest 12 and the power supply 62 is electrically coupled to each of the plurality of ultraviolet light emitters 46. The power supply 62 comprises a rechargeable battery 64 that is integrated into the outer wall 16 of the ice chest 12. A plurality of conductors 66 is provided and respective ones of the plurality of conductors 66 is integrated into the outer wall 16 of the ice chest 12. A respective one of the plurality of conductors 66 is integrated into the bottom wall 14 of the ice chest 12 and a respective one of the plurality of conductors 66 is integrated into the lid 38. Each of the plurality of conductors 66 is comprised of an electrically conductive material and each of the plurality of conductors 66 is electrically coupled to the rechargeable battery 64. The power supply 62 includes a charge port 68 that is recessed into the outer surface 32 of the outer wall 16 of the ice chest 12 thereby facilitating the charge port 68 to insertably receive a charge cord 69. The charge port 68 is electrically coupled to the rechargeable battery 64 for charging the rechargeable battery 64. The power supply 62 includes a power button 70 that is movably integrated into the outer wall 16 of the ice chest 12 and the power button 70 is electrically coupled to each of the plurality of ultraviolet light emitters 46 for actuating or de-actuating the plurality of ultraviolet light emitters 46.

In use, ice, various food items and beverage containers can be stored in the ice chest 12 during a picnic, for example, or other outdoor occasion where food and beverages will be consumed by a group of people. The power button 70 is manipulated to turn on each of the plurality of ultraviolet light emitters 46 for emitting ultraviolet light into the interior of the ice chest 12. In this way the ice, various food items and the beverage containers can be sterilized to inhibit the transfer of bacteria between the people. Thus, the people can safely consume the food items and drink from the beverage containers without becoming ill from a bacterial infection, for example. The charge cord 69 can be plugged into the charge port 68 at any time for recharging the rechargeable battery 64.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A portable food sterilization assembly for containing a sterilizing food items, said assembly comprising:

an ice chest defining an interior space wherein said interior space is configured to contain food items, said ice chest being comprised of a thermally insulating material wherein said ice chest is configured to inhibit thermal communication between said interior space and ambient air, said ice chest having a bottom wall and an outer wall extending upwardly from said bottom wall, said outer wall having a top edge defining an opening in said interior space defined by said ice chest;

a handle having a central member extending between and being perpendicularly oriented with a pair of outward members, each of said outward members having a distal end and a bend being spaced from said distal end such that said distal end of each of said outward members is directed toward each other, said distal end of each of said outward members being rotatably coupled to an outer surface of said outer wall of said ice chest corresponding to a respective one of said first lateral side and said second lateral side of said outer wall, said handle being positionable in a carrying position having said central member being spaced upwardly from said ice chest wherein said central member is configured to be gripped for carrying said ice chest, said handle being positionable in a stored position having said central member resting against said outer wall of said ice chest;

a lid being hingedly coupled to said ice chest, said lid being positionable in a closed position for closing said interior space, said lid being positionable in an open position for exposing said interior space, said lid being comprised of a thermally insulating material wherein said lid is configured to inhibit thermal communication between said interior space and ambient air, said lid having a rear edge and a bottom surface, said rear edge being hingedly coupled to a back side of said top edge of said outer wall of said ice chest;

a plurality of ultraviolet light emitters, respective ones of said plurality of ultraviolet light emitters being integrated into said ice chest wherein each of said respective plurality of ultraviolet light emitters is configured to emit ultraviolet light into said interior space for sterilizing said interior space of said ice chest thereby sterilizing food items contained in said interior space, a respective one of said plurality of ultraviolet light emitters being integrated into said lid wherein said ultraviolet light emitter associated with said lid is configured to emit ultraviolet light into said interior space of said ice chest thereby sterilizing food items contained in said interior space, respective ones of said ultraviolet light emitters associated with said ice chest being integrated into an interior surface of said outer wall, each of said ultraviolet light emitters associated with said outer wall of said ice chest being integrated into a respective one of a front side and a first lateral side and a second lateral side of said outer wall of said ice chest, a respective one of said ultraviolet light emitters associated with said ice chest being integrated into a top surface of said bottom wall of said ice chest, said ultraviolet light emitter associated with said lid being integrated into said bottom surface of said lid;

a plurality of first lenses, each of said plurality of first lenses being integrated into said interior surface of said outer wall of said ice chest, each of said plurality of first lenses being integrated into a respective one of said first lateral side and said second lateral side and said front side of said outer wall of said ice chest such that each of said plurality of first lenses covers a respective one of said plurality of ultraviolet light emitters, each of said first lenses being comprised of a translucent material wherein each of said plurality of first lenses is configured to pass ultraviolet light through said first lenses;

a second lens being integrated into said top surface of said bottom wall of said ice chest such that said second lens covers said ultraviolet light emitter associated with said lid, said second lens being comprised of a translucent material wherein said second lens is configured to pass ultraviolet light through said second lens;

a third lens being integrated into said bottom surface of said lid such that said third lens covers said ultraviolet light emitter associated with said lid, said third lens having a perimeter wall being perpendicularly oriented with said bottom surface of said lid and a distal wall being spaced from and lying on a plane oriented parallel to said bottom surface of said lid, said third lens being comprised of a translucent material wherein said third lens is configured to pass ultraviolet light through said third lens, said perimeter wall being spaced inwardly from a perimeter edge of said lid such that said third lens extends into said interior space of said ice chest when said lid is in said closed position; and a power supply being integrated into said ice chest, said power supply being electrically coupled to each of said plurality of ultraviolet light emitters, said power supply comprising:

a rechargeable battery being integrated into said outer wall of said ice chest;

a plurality of conductors, respective ones of said plurality of conductors being integrated into said outer wall of said ice chest, a respective one of said plurality of conductors being integrated into said bottom wall of said ice chest, a respective one of said plurality of conductors being integrated into said lid, each of said plurality of conductors being comprised of an electrically conductive material, each of said plurality of conductors being electrically coupled to said rechargeable battery;

a charge port being recessed into said outer surface of said outer wall of said ice chest thereby facilitating said charge port to insertably receive a charge cord, said charge port being electrically coupled to said rechargeable battery for charging said rechargeable battery; and a power button being movably integrated into said outer wall of said ice chest, said power button being electrically coupled to each of said plurality of ultraviolet light emitters for actuating or de-actuating said plurality of ultraviolet light emitters.

2. A portable food sterilization assembly for containing a sterilizing food items, said assembly comprising:

an ice chest defining an interior space wherein said interior space is configured to contain food items, said ice chest being comprised of a thermally insulating material wherein said ice chest is configured to inhibit thermal communication between said interior space and ambient air;

a lid being hingedly coupled to said ice chest, said lid being positionable in a closed position for closing said interior space, said lid being positionable in an open position for exposing said interior space, said lid being comprised of a thermally insulating material wherein said lid is configured to inhibit thermal communication between said interior space and ambient air;

a plurality of ultraviolet light emitters, respective ones of said plurality of ultraviolet light emitters being integrated into said ice chest wherein each of said respective plurality of ultraviolet light emitters is configured to emit ultraviolet light into said interior space for sterilizing said interior space of said ice chest thereby sterilizing food items contained in said interior space, a respective one of said plurality of ultraviolet light emitters being integrated into said lid wherein said ultraviolet light emitter associated with said lid is configured to emit ultraviolet light into said interior space of said ice chest thereby sterilizing food items contained in said interior space;

wherein said ice chest has a bottom wall and an outer wall extending upwardly from said bottom wall, said outer wall having a top edge defining an opening in said interior space defined by said ice chest;

wherein said assembly includes a handle having a central member extending between and being perpendicularly oriented with a pair of outward members, each of said outward members having a distal end and a bend being spaced from said distal end such that said distal end of each of said outward members is directed toward each other, said distal end of each of said outward members being rotatably coupled to an outer surface of said outer wall of said ice chest corresponding to a respective one of said first lateral side and said second lateral side of said outer wall, said handle being positionable in a carrying position having said central member being spaced upwardly from said ice chest wherein said central member is configured to be gripped for carrying said ice chest, said handle being positionable in a stored position having said central member resting against said outer wall of said ice chest;

wherein said lid has a rear edge and a bottom surface, said rear edge being hingedly coupled to a back side of said top edge of said outer wall of said ice chest;

said outer wall having said top edge defining an opening in said interior space defined by said ice chest, said outer wall having a first lateral side and a second lateral side and a front side;

wherein respective ones of said ultraviolet light emitters associated with said ice chest is integrated into an interior surface of said outer wall, each of said ultraviolet light emitters associated with said outer wall of said ice chest being integrated into a respective one of said front side and said first lateral side and said second lateral side of said outer wall of said ice chest;

wherein a respective one of said ultraviolet light emitters associated with said ice chest is integrated into a top surface of said bottom wall of said ice chest;

wherein said ultraviolet light emitter associated with said lid being integrated into said bottom surface of said lid;

a power supply being integrated into said ice chest, said power supply being electrically coupled to each of said plurality of ultraviolet light emitters, said power supply comprising:

a rechargeable battery being integrated into said outer wall of said ice chest;

a plurality of conductors, respective ones of said plurality of conductors being integrated into said outer wall of said ice chest, a respective one of said plurality of conductors being integrated into said bottom wall of said ice chest, a respective one of said plurality of conductors being integrated into said lid, each of said plurality of conductors being comprised of an electrically conductive material, each of said plurality of conductors being electrically coupled to said rechargeable battery;

a charge port being recessed into an outer surface of said outer wall of said ice chest thereby facilitating said charge port to insertably receive a charge cord, said charge port being electrically coupled to said rechargeable battery for charging said rechargeable battery; and a power button being movably integrated into said outer wall of said ice chest, said power button being electrically coupled to each of said plurality of ultraviolet light emitters for actuating or de-actuating said plurality of ultraviolet light emitters;

a plurality of first lenses, each of said plurality of first lenses being integrated into said interior surface of said outer wall of said ice chest, each of said plurality of first lenses being integrated into a respective one of said first lateral side and said second lateral side and said front side of said outer wall of said ice chest such that each of said plurality of first lenses covers a respective one of said plurality of ultraviolet light emitters, each of said first lenses being comprised of a translucent material wherein each of said plurality of first lenses is configured to pass ultraviolet light through said first lenses;

a second lens being integrated into said top surface of said bottom wall of said ice chest such that said second lens covers said ultraviolet light emitter associated with said lid, said second lens being comprised of a translucent material wherein said second lens is configured to pass ultraviolet light through said second lens; and a third lens being integrated into said bottom surface of said lid such that said third lens covers said ultraviolet light emitter associated with said lid, said third lens having a perimeter wall being perpendicularly oriented with said bottom surface of said lid and a distal wall being spaced from and lying on a plane oriented parallel to said bottom surface of said lid, said third lens being comprised of a translucent material wherein said third lens is configured to pass ultraviolet light through said third lens, said perimeter wall being spaced inwardly from a perimeter edge of said lid such that said third lens extends into said interior space of said ice chest when said lid is in said closed position.

\* \* \* \* \*